(12) United States Patent
Hedner

(10) Patent No.: US 9,029,324 B2
(45) Date of Patent: *May 12, 2015

(54) SINGLE-DOSE ADMINISTRATION OF FACTOR VIIA

(75) Inventor: Ulla Hedner, Malmo (SE)

(73) Assignee: Novo Nordisk Healthcare AG, Zurich (CH)

( * ) Notice: Subject to any disclaimer, the term of this patent is extended or adjusted under 35 U.S.C. 154(b) by 968 days.

This patent is subject to a terminal disclaimer.

(21) Appl. No.: 12/127,917

(22) Filed: May 28, 2008

(65) Prior Publication Data

US 2008/0261886 A1 Oct. 23, 2008

Related U.S. Application Data

(63) Continuation of application No. 10/196,902, filed on Jul. 16, 2002, now Pat. No. 7,419,949.

(60) Provisional application No. 60/305,720, filed on Jul. 16, 2001.

(51) Int. Cl.
| | | |
|---|---|---|
| A61K 35/14 | (2006.01) |
| A61K 38/36 | (2006.01) |
| A61K 38/48 | (2006.01) |
| C07K 14/745 | (2006.01) |

(52) U.S. Cl.
CPC .................................. *A61K 38/4846* (2013.01)

(58) Field of Classification Search
None
See application file for complete search history.

(56) References Cited

U.S. PATENT DOCUMENTS

| 4,404,132 | A | * | 9/1983 | Mitra ............................ 530/384 |
| 5,180,583 | A | | 1/1993 | Hedner |
| 5,580,560 | A | * | 12/1996 | Nicolaisen et al. ......... 424/94.64 |
| 6,132,730 | A | * | 10/2000 | Thorpe et al. ............... 424/198.1 |
| 6,310,183 | B1 | * | 10/2001 | Johannessen et al. ........ 530/384 |
| 6,833,352 | B2 | * | 12/2004 | Johannessen et al. ....... 514/14.3 |
| 7,015,194 | B2 | * | 3/2006 | Kjalke .......................... 514/14.3 |
| 7,235,638 | B2 | * | 6/2007 | Persson ......................... 530/381 |
| 7,419,949 | B2 | * | 9/2008 | Hedner .......................... 514/1.1 |
| 2006/0025336 | A1 | | 2/2006 | Rojkjaer et al. |

OTHER PUBLICATIONS

Shapiro (A.D. Shapiro, et al. Thromb. Hemost. (1998) 80(5), p. 773-778).*
SN10196902 (now US7419949, Exam. Kosar), Notice of References Cited, Dated: Nov. 16, 2004, Jan. 27, 2005, Oct. 19, 2005, Jul. 24, 2006, and Jul. 31, 2007.*
Shapiro, A.D., et al., Thromb.Hemost, vol. 80(5), pp. 773-778 (1998).
Jaques, L.B. and R.A. Mustard, Biochem J., vol. 34(2), pp. 153-158 (1940).
Lusher, J.M., Eur. J. Haematol. Suppl., vol. 63, pp. 7-10 (1998).
Ingerslev, J., Haematologica, vol. 85 (10 suppl), pp. 15-20 (2000).
Diness, V. et al., Throm. Res., vol. 59, pp. 921-929 (1990).
Butler, K.D., et al., Blood Coag. Fibrin., vol. 4, pp. 459-464 (1993).
Chuansumrit, A. et al., Haemophilia, vol. 6, pp. 61-65 (2000).
Erjardtsen, E., Semin. Thromb. Hemost., vol. 26, pp. 385-391 (2000).
Lusher, J.M. et al., Haemophilia, vol. 4, pp. 790-798 (1998).
Shafi, T. et al., Br. J. Haem., vol. 98, pp. 910-912 (1997).
Poon, M-C et al., Blood, vol. 94, pp. 3951-3953 (1999).
Jurlander, B. et al., Semin. Thromb Hemost., vol. 27, pp. 373-383 (2001).
Negrier, C. and A. Lienhart, blood Coag. Fibrin., vol. 11 (suppl. 1), pp. s-19-s24 (2000).
Petrini, P. and G. Klemetz, Blood Coag. Fibrin., vol. 9 (suppl. 1), pp. s143-s146 (1998).
Inverslev, J. et al., Blood Coag Fibrin. vol. 9 (suppl 1), pp. s07-s110 (1998).
Hay, C.R.M. et al., Thromb Haemost., vol. 78, pp. 1463-1467 (1997).
Hedner, U., Dosing and Monitoring NovoSeven® Treatment, Haemostasis, vol. 26 (suppl. 1), pp. 102-108 (1996).
Lusher, J.M., Haemostasis, vol. 26 (suppl 1), pp. 124-130 (1996).
Kulkami, R. et al., Am. J. Hematol., vol. 67, pp. 240-246 (2001).
"NovoSeven" product insert, Novo Nordisk Pharmaceuticals, Inc. Issued Aug. 2004.
Roberts, II.R., Thoughts on the mechanism of action of FVIIa, $2^{nd}$ Symposium on New Aspects of Hemophilia Treatment, Copenhagen, Denmark 1991, pp. 153-156.
Parameswaran, R. et al., Dose effect and efficacy of rFVIIa in the treatment of haemophilia patients with inhibitors: analysis from the Hemophilia and Thrombosis Research Society Registry, Haemophilia 2005, vol. 11, pp. 100-106.
Mayer, S.A. et al., Recombinant Activated Factor VII for Acute Intracerebral Hemorrhage, New England Journal of Medicine, vol. 352, pp. 777-785 (2005).
Butenas, S. et al., Mechanism of factor VIIa-dependent coagulation in hemophilia blood, Blood, vol. 99, pp. 923-930, Figure a Copyright American Society of Hematology used with permission (2002).
Allen, G.A. et al., The effect of factor X level on thrombin generation and the procoagulant effect of activated factor VII in a cell-based model of coagulation, Blood Coagulation and Fibrinolysis, vol. 11 (suppl 1), pp. 3-7 (2000).
Lindley, C.M. et al., Pharmacokinetics and pharmacodynamics of recombinant Factor VIIa, Clinical Pharmacology & Therapeutics, vol. 55 (6), pp. 638-648 (1994).
Bauer, K.A., Treatment of Factor VII deficiency with recombinant Factor VIIa, Haemostasis, vol. 26 (suppl 1), pp. 155-158 (1996).
Lusher, J. et al., Clinical experience with recombinant Factor VIIa, Blood Coagulation and Fibrinolysis, vol. 9, pp. 119-128 (1998).
Bech, M.R., Recombinant Factor VIIa in Joint and Muscle Bleeding Episodes, Haemostasis, vol. 26 (suppl 1), pp. 155-158 (1996).
Lusher, J.M..: Recombinant Factor VIIa (NovoSeven ®) in the Treatment of Internal Bleeding in Patients with Factor VIII and IX Inhibitors, Haemostasis 1996; 26 (suppl 1): 124-130.

(Continued)

*Primary Examiner* — Maury Audet
(74) *Attorney, Agent, or Firm* — Jianjie Hu

(57) ABSTRACT

The present invention provides methods for preventing and/or treating bleeding episodes by administering a single dose of a Factor VIIa equivalent. Preferably, the single dose comprises between about 150 and about 500 ug/kg Factor VIIa equivalent.

9 Claims, No Drawings

(56) References Cited

OTHER PUBLICATIONS

Lusher, J.M, et al.: A randomized, double-blind comparison of two dosage levels of recombinant factor VIIa in the treatment of joint, muscle and mucocutaneous haemorrhages in persons with hemophilia A and B, with and without inhibitor, Haemophilia 1998; 4: 790-798.

Shapiro, A.D., et al: Prospective, Randomised Trial of Two Doses of rFVIIa (NovoSeven) in Haemophilia Patients with Inhibitors Undergoing Surgery, Thrombosis and Haemostasis 1998; 80: 773-778.

Novo Nordisk Pharmaceuticals, Inc., "Novoseven Product Insert", 2006.

Abshire, "Dose Optimization of Recombinant Factor VIIa for Control of Mild to Moderate Bleeds in Inhibitor Patients: Improved Efficacy with Higher Dosing," Seminars in Hematology, vol. 41, No. 1, Suppl 1, 2004, pp. 3-7.

\* cited by examiner

SEQUENCE LISTING

<160> NUMBER OF SEQ ID NOS: 1

<210> SEQ ID NO 1
<211> LENGTH: 406
<212> TYPE: PRT
<213> ORGANISM: Homo sapiens
<220> FEATURE:
<221> NAME/KEY: MISC_FEATURE
<222> LOCATION: (1)..(406)
<223> OTHER INFORMATION: Xaa= 4-carboxyglutamic acid
      (gamma-carboxyglutamate)

<400> SEQUENCE: 1

Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr

-continued

```
                340                 345                 350
Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
        370                 375                 380

Glu Trp Leu Gln Lys Leu Met Arg Ser Glu Pro Arg Pro Gly Val Leu
385                 390                 395                 400

Leu Arg Ala Pro Phe Pro
                405
```

SINGLE-DOSE ADMINISTRATION OF FACTOR VIIA

CROSS REFERENCE TO RELATED APPLICATIONS

This application is a continuation of U.S. application Ser. No. 10/196,902 filed Jul. 16, 2002 (which has been allowed on Feb. 22, 2008) and claims priority under 35 U.S.C. 119 of U.S. application Ser. No. 60/305,720 filed on Jul. 16, 2001, the contents of which are fully incorporated herein by reference.

FIELD OF THE INVENTION

The present invention relates to methods for preventing and/or treating bleeding using coagulation factors.

BACKGROUND OF THE INVENTION

Factor VII is a plasma coagulation factor, which, once activated to Factor VIIa, initiates the normal haemostatic process by forming a complex with tissue factor (TF), a cell surface glycoprotein that is exposed to the circulation as a result of injury to the vessel wall. Subsequently, the Factor VIIa-TF complex activates Factor IX and Factor X into their activated forms (Factor IXa and Factor Xa, respectively). Factor Xa converts limited amounts of prothrombin to thrombin on the tissue factor-bearing cell. Thrombin activates platelets and Factors V and VIII into Factors Va and VIIIa, both cofactors in the further process leading to the full thrombin burst. Thrombin finally converts fibrinogen to fibrin resulting in formation of a fibrin clot. Fibrin clots formed in the presence of high thrombin concentrations comprise a tighter network and are more resistant to proteolysis than clots formed in lower concentrations of thrombin. Accordingly, a full thrombin burst is likely to be important for forming a hemostatic plug that is resistant to fibrinolysis and thus to facilitate full hemostasis and wound healing.

Factor VIIa, as well as Factor VIII and Factor IX, have been used to control bleeding disorders that are caused by clotting factor deficiencies (such as, e.g. haemophilia A and B or deficiency of coagulation Factors XI or VII) or clotting factor inhibitors. Factor VIIa has also been used to control excessive bleeding caused by defective platelet function, thrombocytopenia or von Willebrand's disease.

Typically, however, patients are treated with multiple injections or infusions of a coagulation factor before the bleeding is stopped. In the case of Factor VIII and Factor IX administration, a considerable number of injections are needed to maintain haemostasis until the injury causing the bleeding is completely healed. A quicker and more effective treatment, as well as a reduction in the number of injections needed before the bleeding is stopped, represent important benefit to such patients. It would also be a considerable benefit to a patient needing frequent injections or infusions with a haemostatic agent that the injection frequency be reduced.

Thus, there is a need in the art for methods for preventing and/or treating bleeding episodes that reduce the duration of administration and provide a more rapid hemostasis.

SUMMARY OF THE INVENTION

The present invention relates to methods for preventing and/or treating a bleeding episode in a subject in need of such treatment, which are carried out by administering to the subject, in a single dose, a single-dose-effective amount of Factor VIIa or a Factor VIIa equivalent. Preferably, subsequent to the administration, no further Factor VIIa or protein having Factor VIIa coagulant activity is administered to the subject for an interval of at least about 1 hour. In some embodiments, the interval is at least about 4 hours; in other embodiments, the interval is at least about 24 hours; and in some embodiments, no further Factor VIIa or protein having Factor VIIa coagulant activity is administered during the particular bleeding episode that is being treated.

In some embodiments, the single-dose-effective amount comprises between about 150 and about 500 ug/kg Factor VIIa or a corresponding amount of a Factor VIIa equivalent; in other embodiments, the single-dose-effective amount comprises between about 200 and about 500 ug/kg; between about 250 and about 500 ug/kg; between about 300 and about 500 ug/kg; between about 350 and 500 ug/kg; between about 400 and about 500 ug/kg; between about 450 and about 500 ug/kg; and greater than 500 ug/kg, respectively, of Factor VIIa or a corresponding amount of a Factor VIIa equivalent.

In some embodiments, the Factor VIIa equivalent exhibits at least about 30% of the coagulant activity of Factor VIIa on a molar basis. Non-limiting examples of a Factor VIIa equivalent include S52A-FVII, S60A-FVII; L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII; Factor VIIa variants exhibiting increased proteolytic stability as disclosed in U.S. Pat. No. 5,580,560; Factor VIIa that has been proteolytically cleaved between residues 290 and 291 or between residues 315 and 316; oxidized forms of Factor VIIa; Factor VII-sequence variants wherein the amino acid residue in positions 290 and/or 291 (of SEQ ID NO:1), preferably 290, have been replaced, and Factor VII-sequence variants wherein the amino acid residue in positions 315 and/or 316 (of SEQ ID NO:1), preferably 315, have been replaced.

In some embodiments, the method further comprises administering, with or substantially simultaneously with the single dose, a second coagulant agent. Non-limiting examples of a second coagulant agent include Factor VIII, Factor IX, and Factor XIII.

In some embodiments, the invention provides a method for treating a bleeding episode, which is carried out by administering to a subject in need of such treatment (i) a first amount of Factor VIIa or a Factor VIIa equivalent and (ii) a second amount of second coagulant agent, wherein the first and second amounts together comprise an aggregate effective amount for treating the bleeding episode and the aggregate effective amount is administered in a single dose.

In some embodiments, the Factor VIIa used in practicing the invention is recombinant human Factor VIIa.

In one embodiment, the invention provides a method for treating a bleeding episode, which is carried out by administering to a human subject in need of such treatment an effective amount for treating said bleeding of human Factor VIIa or a human Factor VIIa equivalent, wherein:

(i) said effective amount is administered in a single dose over a period of less than about 5 minutes;

(ii) said effective amount comprises between about 300 and about 500 ug/kg human Factor VIIa or human Factor VIIa equivalent or a corresponding amount of a Factor VIIa equivalent; and (iii) subsequent to said administration, no further Factor VIIa or Factor VIIa equivalent is administered to said subject for a period of at least about 1 hour.

In practicing the present invention, administration may be achieved by any mode of administration, including, without limitation, intravenous, intramuscular, subcutaneous, mucosal, and pulmonary routes of administration.

In another aspect, the invention provides a method for preventing a bleeding episode, which is carried out by administering to a human subject in need of such prevention an effective amount for preventing the bleeding episode of human Factor VIIa or a human Factor VIIa equivalent, wherein:

(i) the effective amount is administered in a single dose over a period of less than about 5 minutes;

(ii) the effective amount comprises between about 250 and about 500 ug/kg human Factor VIIa or human Factor VIIa equivalent or a corresponding amount of a Factor VIIa equivalent; and (iii) subsequent to the administration, no further Factor VIIa or Factor VIIa equivalent is administered to said subject for a period of at least about 1 hour.

In some embodiments, the subject suffers from hemophilia A or B.

In some embodiments, the bleeding is joint bleeding.

In some embodiments, the subject has not been treated therapeutically with an anticoagulant for at least about 48 hours prior to administration of Factor VIIa or a Factor VIIa equivalent.

In some embodiments, the subject has not been treated therapeutically with a Vitamin K antagonist for at least about 48 hours prior to said administering.

DETAILED DESCRIPTION OF THE INVENTION

The present invention relates to methods for preventing and/or treating bleeding in animals, particularly in humans. The invention is based on the discovery that administration of a single dose comprising a predetermined amount of Factor VIIa is effective in treating bleeding episodes, including major bleeding episodes, and can also be used to prevent an anticipated bleeding episode.

Without wishing to be bound by theory, it is believed that Factor VIIa enhances thrombin generation on tissue factor-bearing cells and on activated platelets at the site of injury and that administration of a single dose of Factor VIIa according to the present invention provides a full thrombin burst, thereby facilitating the formation of a tight, strong fibrin network that is relatively resistant to premature fibrinolysis and obviating the need for further administration of Factor VIIa.

As used herein, prevention refers to prophylactic administration of Factor VIIa so as to minimize or inhibit an anticipated bleeding episode, such as, e.g., prior to surgery. Treatment refers to regulation of an already-occurring bleeding, such as, for example, in trauma, with the purpose of inhibiting or minimizing the bleeding. It will be understood that efficacy in prevention and/or treatment according to the present invention encompasses the absence of significant side-effects, including, without limitation, disseminated intravascular coagulation (DIC), that would counterindicate to those of ordinary skill in the art the use of any particular therapeutic regimen.

Bleeding refers to extravasation of blood from any component of the circulatory system. The term "bleeding episode" includes, without limitation, bleeding (including, without limitation, excessive, uncontrolled bleeding, i.e., haemorrhaging) in connection with surgery or trauma, such as, for example, in connection with acute haemarthroses (bleedings in joints), chronic haemophilic arthropathy, haematomas, (e.g., muscular, retroperitoneal, sublingual and retropharyngeal), bleedings in other tissue, haematuria (bleeding from the renal tract), cerebral haemorrhage, surgery (e.g., hepatectomy), dental extraction, and gastrointestinal bleedings (e.g., UGI bleeds). Also included are hemorrhages in organs such as the brain, inner ear region and eyes with limited possibility for surgical haemostasis; as well as hemorrhages in connection with biopsies of various organs (liver, lung, tumour tissue, gastrointestinal tract) as well as laparoscopic surgery. Common to these situations is the difficulty in providing haemostasis using surgical techniques (such as, e.g., sutures or clips), which is also the case when bleeding is diffuse.

In practicing the invention, Factor VIIa or a Factor VIIa equivalent is administered to a patient as a single dose comprising a single-dose-effective amount. Administration of a single dose refers to administration of an entire dose of Factor VIIa as a bolus over a period of less than about 5 minutes. In some embodiments, the administration occurs over a period of less than about 2.5 minutes, and, in some, over less than about 1 min.

A single-dose-effective amount of Factor VIIa or a Factor VIIa equivalent refers to the amount of Factor VIIa or equivalent which, when administered in a single dose according to the invention, produces a measurable improvement in at least one clinical parameter of haemostasis known to those of ordinary skill in the art (see below). Typically, a single-dose effective amount comprises at least 150 ug/kg Factor VIIa. In different embodiments, a single-dose-effective amount of Factor VIIa comprises between about 150-500 ug/kg; 250-500 ug/kg; 300-500 ug/kg; 350-500 ug/kg; 400-500 ug/kg; 450-500 ug/kg; or more than 500 ug/kg, respectively. When Factor VIIa equivalents are administered according to the present invention, a single-dose effective amount corresponding to the above-cited amounts may be determined by comparing the anticoagulant activity of the Factor VIIa equivalent with that of Factor VIIa (see below) and adjusting the amount to be administered proportionately.

It will be understood that a single-dose-effective amount of Factor VIIa may vary according to the subject's haemostatic status, which, in turn, may be reflected in one or more clinical parameters, including, e.g., relative levels of circulating coagulation factors; amount of blood lost; rate of bleeding; hematocrit, and the like. It will be further understood that the single-dose-effective amount may be determined by those of ordinary skill in the art by routine experimentation, by constructing a matrix of values and testing different points in the matrix.

In some embodiments, following administration of a single-dose of Factor VIIa or a Factor VIIa equivalent according to the invention, the patient receives no further Factor VIIa or Factor VIIa equivalent for an interval of at least about 1 hour. In some embodiments the post-administration interval is at least about 4 hours; in other embodiments, the post-administration interval is at least about 24 hours. In still other embodiments, no further Factor VIIa or Factor VIIa equivalent is administered to treat the particular bleeding episode.

According to the invention, Factor VIIa or a Factor VIIa equivalent may be administered by any effective route, including, without limitation, intravenous, intramuscular, subcutaneous, mucosal, and pulmonary routes of administration. Preferably, administration is by an intravenous route.

Factor VIIa and Factor VIIa Equivalents:

In practicing the present invention, any Factor VIIa or equivalent may be used that is effective in preventing or treating bleeding when administered in a single dose. In some embodiments, the Factor VIIa is human Factor VIIa, as disclosed, e.g., in U.S. Pat. No. 4,784,950 (wild-type Factor VII). The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa.

Factor VIIa equivalents include, without limitation, Factor VII polypeptides that have either been chemically modified relative to human Factor VIIa and/or contain one or more amino acid sequence alterations relative to human Factor VIIa. Such equivalents may exhibit different properties relative to human Factor VIIa, including stability, phospholipid binding, altered specific activity, and the like.

In one series of embodiments, a Factor VIIa equivalent includes polypeptides that exhibit at least about 10%, preferably at least about 30%, more preferably at least about 50%, and most preferably at least about 70%, of the specific biological activity of human Factor VIIa. For purposes of the invention, Factor VIIa biological activity may be quantified by measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by (i) measuring the ability of Factor VIIa or a Factor VIIa equivalent to produce of Factor Xa in a system comprising TF embedded in a lipid membrane and Factor X. (Persson et al., *J. Biol. Chem.* 272:19919-19924, 1997); (ii) measuring Factor X hydrolysis in an aqueous system (see, Example 5 below); (iii) measuring the physical binding of Factor VIIa or a Factor VIIa equivalent to TF using an instrument based on surface plasmon resonance (Persson, *FEBS Letts.* 413:359-363, 1997) and (iv) measuring hydrolysis of a synthetic substrate by Factor VIIa and/or a Factor VIIa equivalent.

Non-limiting examples of Factor VII-related polypeptides having substantially the same or improved biological activity as wild-type Factor VII include S52A-FVII, S60A-FVII (Iino et al., *Arch. Biochem. Biophys.* 352: 182-192, 1998); L305V-FVII, L305V/M306D/D309S-FVII, L305I-FVII, L305T-FVII, F374P-FVII, V158T/4298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII; Factor VIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., *Biotechnol. Bioeng.* 48:501-505, 1995); oxidized forms of Factor VIIa (Kornfelt et al., *Arch. Biochem. Biophys.* 363:43-54, 1999), Factor VII-sequence variants wherein the amino acid residue in positions 290 and/or 291 (of SEQ ID NO:1), preferably 290, have been replaced, and Factor VII-sequence variants wherein the amino acid residue in positions 315 and/or 316 (of SEQ ID NO:1), preferably 315, have been replaced.

Preparations and Formulations:

The present invention encompasses therapeutic administration of Factor VIIa or Factor VIIa equivalents, which is achieved using formulations that comprise Factor VIIa preparations. As used herein, a "Factor VII preparation" refers to a plurality of Factor VIIa polypeptides or Factor VIIa equivalent polypeptides, including variants and chemically modified forms, that have been separated from the cell in which they were synthesized, whether a cell of origin or a recombinant cell that has been programmed to synthesize Factor VIIa or a Factor VIIa equivalent.

Separation of polypeptides from their cell of origin may be achieved by any method known in the art, including, without limitation, removal of cell culture medium containing the desired product from an adherent cell culture; centrifugation or filtration to remove non-adherent cells; and the like.

Optionally, Factor VII polypeptides may be further purified. Purification may be achieved using any method known in the art, including, without limitation, affinity chromatography, such as, e.g., on an anti-Factor VII antibody column (see, e.g., Wakabayashi et al., *J. Biol. Chem.* 261:11097, 1986; and Thim et al., *Biochem.* 27:7785, 1988); hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, *Protein Purification*, Springer-Verlag, New York, 1982; and *Protein Purification*, J.-C. Janson and Lars Ryden, editors, VCH Publishers, New York, 1989. Following purification, the preparation preferably contains less than about 10% by weight, more preferably less than about 5% and most preferably less than about 1%, of non-Factor VII proteins derived from the host cell.

Factor VII and Factor VII-related polypeptides may be activated by proteolytic cleavage, using Factor XIIa or other proteases having trypsin-like specificity, such as, e.g., Factor IXa, kallikrein, Factor Xa, and thrombin. See, e.g., Osterud et al., *Biochem.* 11:2853 (1972); Thomas, U.S. Pat. No. 4,456,591; and Hedner et al., *J. Clin. Invest.* 71:1836 (1983). Alternatively, Factor VII may be activated by passing it through an ion-exchange chromatography column, such as Mono Q® (Pharmacia) or the like. The resulting activated Factor VII may then be formulated and administered as described below.

Pharmaceutical compositions or formulations for use in the present invention comprise a Factor VIIa preparation in combination with, preferably dissolved in, a pharmaceutically acceptable carrier, preferably an aqueous carrier or diluent. A variety of aqueous carriers may be used, such as water, buffered water, 0.4% saline, 0.3% glycine and the like. The preparations of the invention can also be formulated into liposome preparations for delivery or targeting to the sites of injury. Liposome preparations are generally described in, e.g., U.S. Pat. Nos. 4,837,028, 4,501,728, and 4,975,282. The compositions may be sterilised by conventional, well-known sterilisation techniques. The resulting aqueous solutions may be packaged for use or filtered under aseptic conditions and lyophilised, the lyophilised preparation being combined with a sterile aqueous solution prior to administration.

The compositions may contain pharmaceutically acceptable auxiliary substances or adjuvants, including, without limitation, pH adjusting and buffering agents and/or tonicity adjusting agents, such as, for example, sodium acetate, sodium lactate, sodium chloride, potassium chloride, calcium chloride, etc.

Combinations:

The present invention encompasses combined single-dose administration of an additional agent in concert with Factor VIIa or a Factor VIIa equivalent. In some embodiments, the additional agent comprises a coagulant, including, without limitation, a coagulation factor such as, e.g., Factor VIII, Factor IX, or Factor XIII; or an inhibitor of the fibrinolytic system, such as, e.g., aprotinin, ε-aminocaproic acid or tranexamic acid. In other embodiments, the additional agent comprises an anticoagulant, including, without limitation, heparin, warfarin, coumarin, and modified Factor VII polypeptides, such as, e.g., R152E-Factor VIIa (Wildgoose et al., *Biochem* 29:3413-3420, 1990), S344A-Factor VIIa (Kazama et al., *J. Biol. Chem.* 270:66-72, 1995), FFR-Factor VIIa (Holst et al., *Eur. J. Vasc. Endovasc. Surg.* 15:515-520, 1998), Factor VIIa lacking the Gla domain, (Nicolaisen et al., *FEBS Letts.* 317:245-249, 1993), and chemically modified Factor VII polypeptides (U.S. Pat. No. 5,997,864).

It will be understood that, in embodiments comprising single-dose administration of combinations of Factor VIIa with other agents, the dosage of Factor VIIa or Factor VIIa equivalent may on its own comprise a single-dose-effective amount. Alternatively, the combination of Factor VIIa or equivalent and the second agent may together comprise a single-dose-effect amount for preventing or treating bleeding episodes.

Indications:

The present invention encompasses single-dose administration of Factor VIIa or a Factor VIIa equivalent to any patient who either anticipates a bleeding episode or who is actively experiencing a bleeding episode. Such patients include, without limitation, those suffering from bleeding disorders that are caused by clotting factor deficiencies (e.g. haemophilia A and B, or deficiency of coagulation Factors XI or VII); clotting factor inhibitors; defective platelet function; thrombocytopenia; or von Willebrand's disease. The methods of the invention may also be applied to patients who are about to undergo surgery, preferably major surgery, whether or not they suffer from a bleeding disorder; as well as trauma patients. Furthermore, any type of profuse bleeding from the gastrointestinal tract, or any bleeding occurring postoperatively (including that occurring in patients not suffering from a bleeding disorder) may benefit from treatment according to the present invention.

In some embodiments, the invention does not encompass administration of Factor VIIa or equivalent to patients undergoing minor surgery. In other embodiments, the invention does not encompass administration of Factor VIIa or equivalent to patients not suffering from a clotting disorder who had been administered an anticoagulant (such as, e.g., acetocoumerol) within 48 hours prior to Factor VIIa administration. In other embodiments, the invention does not encompass administration of Factor VIIa or equivalent to patients not suffering from a clotting disorder who had been administered a Vitamin K antagonist within 48 hours prior to Factor VIIa administration.

The present invention also provides the benefit of allowing a patient to self-administer an effective dose of Factor VIIa or a Factor VIIa equivalent in order to facilitate effective management of anticipated or current bleeding episodes.

Many variations of the present invention will suggest themselves to those skilled in the art in light of the above detailed description. Such obvious variations are within the full intended scope of the invention.

All patents, patent applications, and literature references referred to herein are hereby incorporated by reference in their entirety.

The following examples are intended as non-limiting illustrations of the present invention.

Example 1

High-Dose Factor VIIa Administration

Patients suffering from hemophilia (including, e.g., patients with clotting factor inhibitors, acquired inhibitor patients, patients suffering from Factor VII deficiency, and patients suffering from von Willebrands disease) are enrolled in a registry that tracks the outcome of bleeding episodes whose treatment includes bolus administration of Factor VIIa.

The bleeding episodes are characterized as spontaneous, related to traumatic injury, or other (including, e.g., surgical or dental procedures). The dosage groups are characterized as <100 ug/kg; 100-150 ug/kg; 150-200 ug/kg; and >200 ug/kg. Responses to treatment (as assessed at 72 h) are characterized as cessation of bleeding, slowing of bleeding; or no response.

Example 2

Single High-Dose Factor VIIa Administration

Description of Clinical Trial:

A randomized, multicenter, cross-over, double-blind study is performed to evaluate the efficacy and safety of Factor VIIa (by two different blinded dose schedules) in producing hemostasis in joint bleeds in a home-treatment setting. Subjects with congenital hemophilia A or B and inhibitors to Factor VIII or Factor IX receive treatment and are assessed for at least 9 hours after the dosing. The success or failure of the treatment is ascertained using a pilot algorithm to assess changes in pain and joint mobility. rFVIIa will be given as an intravenous bolus injection, either at 270 µg/kg body weight dose at hour 0, or at 90 µg/kg body weight doses given at hours 0, 3 and 6 and placebo solutions will be administered to blind subject as to the dose regimen of rFVIIa being administered. If additional doses of Factor VIIa are administered within the first 9 hours to achieve hemostasis, then the treatment efficacy is graded as a failure.

Trial Population:

Twenty-four patients with congenital hemophilia A or B and inhibitors to factor VIII or IX have been enrolled in this trial. Patients must have experienced two or more mild or moderate joint bleeds during the past 12 months.

Assessments

Treatment efficacy is based on the evaluation of pain, joint mobility and measure of circumference of the elbow or knee at the midpoint of the joint in extension. These variables are graded and entered in the diary by the patient/caregiver. Pain and mobility are assessed as more, no difference or less than before the treatment and circumference is measured in millimeters. An independent blinded committee reviews the diary data on pain and joint mobility and judges the response to treatment as success or failure based on a pilot algorithm developed for this study.

The invention claimed is:

1. A method for treating a bleeding episode in a subject in need of such treatment, said method comprising administering intravenously to said subject a purified Factor VIIa equivalent, wherein said administering is in a single dose and said dose comprises a single-dose-effective amount of said Factor VIIa equivalent wherein said single-dose-effective amount comprises between 250 and 500 µg/kg Factor VIIa equivalent, and wherein, subsequent to said administration, no further Factor VIIa equivalent is administered to said subject for a period of at least 4 hours, wherein said Factor VIIa equivalent exhibits at least about 30% of the coagulant activity of Factor VIIa on a molar basis, and wherein said Factor VIIa equivalent is a Factor VII polypeptide that has been chemically modified relative to human Factor VIIa and/or contains one or more amino acid sequence alterations relative to human Factor VIIa.

2. A method as defined in claim 1, wherein said period is at least about 24 hours.

3. A method as defined in claim 1, wherein said single dose is administered over a period of less than about 5 minutes.

4. A method as defined in claim 1, wherein said single-dose-effective amount comprises between about 300 and about 500 µg/kg Factor VIIa equivalent.

5. A method as defined in claim 1, wherein said Factor VIIa equivalent is selected from the group consisting of: S52A-FVII, S60A-FVII; L305-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, K157A-FVII, E296V-FVII, E296V/M298Q-FVII, V158D/E296V-FVII, V158D/M298K-FVII, and S336G-FVII; Factor VIIa that has been proteolytically cleaved between residues 290 and 291; Factor VIIa that has been proteolytically cleaved between residues 315 and 316; and oxidized forms of Factor VIIa.

6. A method as defined in claim 1, further comprising administering, in said single dose, or substantially simultaneously with said single dose, a second coagulant agent.

7. A method as defined in claim 6, wherein said second coagulant agent is selected from the group consisting of Factor VII, Factor VIII, Factor IX, and Factor XIII.

8. A method as defined in claim 1, further comprising administering an anticoagulant, wherein said anticoagulant is administered in said single dose, or substantially simultaneously with said single dose.

9. A method for treating a bleeding episode, said method comprising administering to a subject in need of such treatment (i) a first amount of a Factor VIIa equivalent and (ii) a second amount of second coagulant agent, wherein said first amount comprises between 250 and 500 µg/kg Factor VIIa equivalent and wherein said first and second amounts together comprise an aggregate effective amount for treating said bleeding and said aggregate effective amount is administered in a single dose, and wherein, subsequent to said administration, no further Factor VIIa equivalent is administered to said subject for a period of at least 4 hours, wherein said Factor VIIa equivalent exhibits at least about 30% of the coagulant activity of Factor VIIa on a molar basis, and wherein said Factor VIIa equivalent is a Factor VII polypeptide that has been chemically modified relative to human Factor VIIa and/or contains one or more amino acid sequence alterations relative to human Factor VIIa.

* * * * *